(12) United States Patent
Hasan et al.

(10) Patent No.: US 10,636,437 B2
(45) Date of Patent: Apr. 28, 2020

(54) SYSTEM AND METHOD FOR MONITORING DIETARY ACTIVITY

(71) Applicant: Robert Bosch GmbH, Stuttgart (DE)

(72) Inventors: Taufiq Hasan, Syosset, NY (US); Shabnam Ghaffarzadegan, San Mateo, CA (US); Zhe Feng, Mountain View, CA (US)

(73) Assignee: Robert Bosche GmbH, Stuttgart (DE)

( * ) Notice: Subject to any disclaimer, the term of this patent is extended or adjusted under 35 U.S.C. 154(b) by 0 days.

(21) Appl. No.: 16/284,309

(22) Filed: Feb. 25, 2019

(65) Prior Publication Data

US 2019/0272845 A1   Sep. 5, 2019

Related U.S. Application Data

(60) Provisional application No. 62/637,800, filed on Mar. 2, 2018.

(51) Int. Cl.
*G10L 25/51* (2013.01)
*G16H 20/60* (2018.01)
(Continued)

(52) U.S. Cl.
CPC ............ *G10L 25/51* (2013.01); *A61B 5/4205* (2013.01); *A61B 5/6822* (2013.01);
(Continued)

(58) Field of Classification Search
None
See application file for complete search history.

(56) References Cited

U.S. PATENT DOCUMENTS

| 2009/0227907 A1* | 9/2009 | Kandori | A61B 5/11 600/593 |
| 2014/0275748 A1* | 9/2014 | Dunki-Jacobs | A61B 5/4839 600/37 |

(Continued)

FOREIGN PATENT DOCUMENTS

WO   2014159749 A1   10/2014

OTHER PUBLICATIONS

Kalantarian, Haik; Alshurafa, Nabil; Pourhomayoun, Mohammad; Sarin, Shruti; Le, Tuan; and Sarrafzadeh, Majid, Spectrogram-Based Audio Classification of Nutrition Intake, 2014 Health Innovations and Point-of-Care Technologies Conference, Seattle, Washington USA, Oct. 8-10, 2014, pp. 161-164.

(Continued)

*Primary Examiner* — Paul W Huber
(74) *Attorney, Agent, or Firm* — Maginot, Moore & Beck LLP

(57) ABSTRACT

A system for monitoring dietary activity of a user includes a wearable device having at least one audio input unit configured to record an audio sample corresponding to audio from a user's neck. The system further includes a processor configured to execute programmed instructions stored in a memory to obtain an audio sample from the audio input unit of a wearable device, determine segmental feature values of a set of selected features from the audio sample by extracting short-term features in the set of selected features from the audio sample and determining the segmental feature values of the set of selected features from the extracted short-term features. The processor is further configured to, using a classifier, classify a dietary activity based on the determined segmental feature values of the audio sample and generate an output corresponding to the classified dietary activity.

20 Claims, 8 Drawing Sheets

(51) Int. Cl.

| | | |
|---|---|---|
| *H04R 29/00* | (2006.01) | |
| *G10L 25/21* | (2013.01) | |
| *H04R 1/08* | (2006.01) | |
| *A61B 5/00* | (2006.01) | |
| *A61B 7/00* | (2006.01) | |
| *H04R 1/46* | (2006.01) | |
| *G10L 25/66* | (2013.01) | |
| *H04R 19/04* | (2006.01) | |
| *H04R 19/01* | (2006.01) | |

(52) U.S. Cl.
CPC ............ *A61B 5/7267* (2013.01); *A61B 7/003* (2013.01); *A61B 7/008* (2013.01); *G10L 25/21* (2013.01); *G10L 25/66* (2013.01); *G16H 20/60* (2018.01); *H04R 1/08* (2013.01); *H04R 1/46* (2013.01); *H04R 29/00* (2013.01); *H04R 19/01* (2013.01); *H04R 19/04* (2013.01); *H04R 2201/003* (2013.01)

(56) References Cited

U.S. PATENT DOCUMENTS

| | | | |
|---|---|---|---|
| 2016/0073953 A1 | 3/2016 | Sazonov | |
| 2016/0302003 A1* | 10/2016 | Rahman | .................... H04R 1/46 |
| 2018/0242908 A1* | 8/2018 | Sazonov | .............. A61B 5/4866 |

OTHER PUBLICATIONS

Amft, Oliver and Tröster, Gerhard, On-Body Sensing Solutions for Automatic Dietary Monitoring, IEEE Pervasive computing, vol. 8, No. 2, 2009, pp. 62-70.

Makeyev, O.; Lopez-Meyer, P.; Schuckers, S.; Besio, W.; and Sazonov, E., Automatic food intake detection based on swallowing sounds, Biomedical Signal Processing and Control, vol. 7, No. 6, 2012, pp. 649-656.

Shuzo, M.; Lopez, G.; Takashima, T.; Komori, S.; Delaunay, J.-J.; and Yamada, I., Discrimination of Eating Habits with a Wearable Bone Conduction Sound Recorder System, IEEE Sensors 2009 Conference, pp. 1666-1669.

Kalantarian, H.; Mortazavi, B.; Alshurafa, N.; Sideris, C.; Le, T.; and Sarrafzadeh, M., A comparison of piezoelectric-based inertial sensing and audio-based detection of swallows, Obesity Medicine, vol. 1, pp. 6-14, 2016.

Cheng, J.; Zhou, B.; Kunze, K; Rheinländer, C. C.; Wille, S.; Wehn, N.; Weppner, J.; and Lukowicz, P., Activity Recognition and Nutrition Monitoring in Every Day Situations with a Textile Capacitive Neckband, Procedings of the 2013 ACM conference on Pervasive and ubiquitous computing adjunct publication, ACM, 2013, pp. 155-158.

Kong, F. and Tan, J., DietCam: Automatic dietary assessment with mobile camera phones, Pervasive and Mobile Computing, vol. 8, No. 1, pp. 147-163, 2012.

Yatani, K. and Truong, K. N., BodyScope: A Wearable Acoustic Sensor for Activity Recognition, Proceedings of the 2012 ACM Conference on Ubiquitous Computing, ACM, 2012, pp. 341-350.

Sazonov, E and Fontana, J. M., A Sensor System for Automatic Detection of Food Intake Through Non-Invasive Monitoring of Chewing, IEEE Sensors Journal, vol. 12, No. 5, pp. 1340-1348, 2012.

Rahman, T.; Adams, A. T.; Zhang, M.; Cherry, E; Zhou, B.; Peng, H.; and Choudhury, T., BodyBeat: A Mobie System for Sensing Non-Speech Body Sounds, MobiSys, vol. 14, 2014, pp. 2-13.

Kira, K. and Rendell, L. A. The Feature Selection Problem: Traditional Methods and a New Algorithm, AAAI-92 Proceedings, vol. 2, 1992, pp. 129-134.

Campbell, W. M.; Campbell, J. P.; Reynolds, D. A.; Singer, E; and Torres-Carrasquillo, P. A., Support vector machines for speaker and language recognition, Computer Speech and Language, 20 (2006), pp. 210-229.

Quinlan, J. R., Bagging, Boosting, and C4.5, AAAI-96 Proceedings, vol. 1, pp. 725-730, 1996.

Sen, S.; Subbaraju, V.; Misra, A.; Balan, R. K; and Lee, Y., The Case for Smartwatch-based Diet Monitoring, Workshop on Sensing Systems and Applications Using Wrist Worn Smart Devices, 2015, pp. 585-590.

Ravi, D.; Lo, B.; and Yang, G.-Z., Real-time Food Intake Classification and Energy Expenditure Estimation on a Mobile Device, 2015 IEEE 12th International Conference on Wearable and Implantable Body Sensor Networks (BSN), 2015, pp. 1-6.

Nishimura, J. and Kuroda, T., Eating habits monitoring using wireless wearable in-ear microphone, 2008 3rd International Symposium on Wireless Pervasive Computing, 2008. ISWPC 2008, pp. 130-132.

Dacremont, C.; Spectral Composition of Eating Sounds Generated by Crispy, Crunchy and Crackly Foods, Journal of Texture Studies, vol. 26, pp. 27-43, 1995.

* cited by examiner

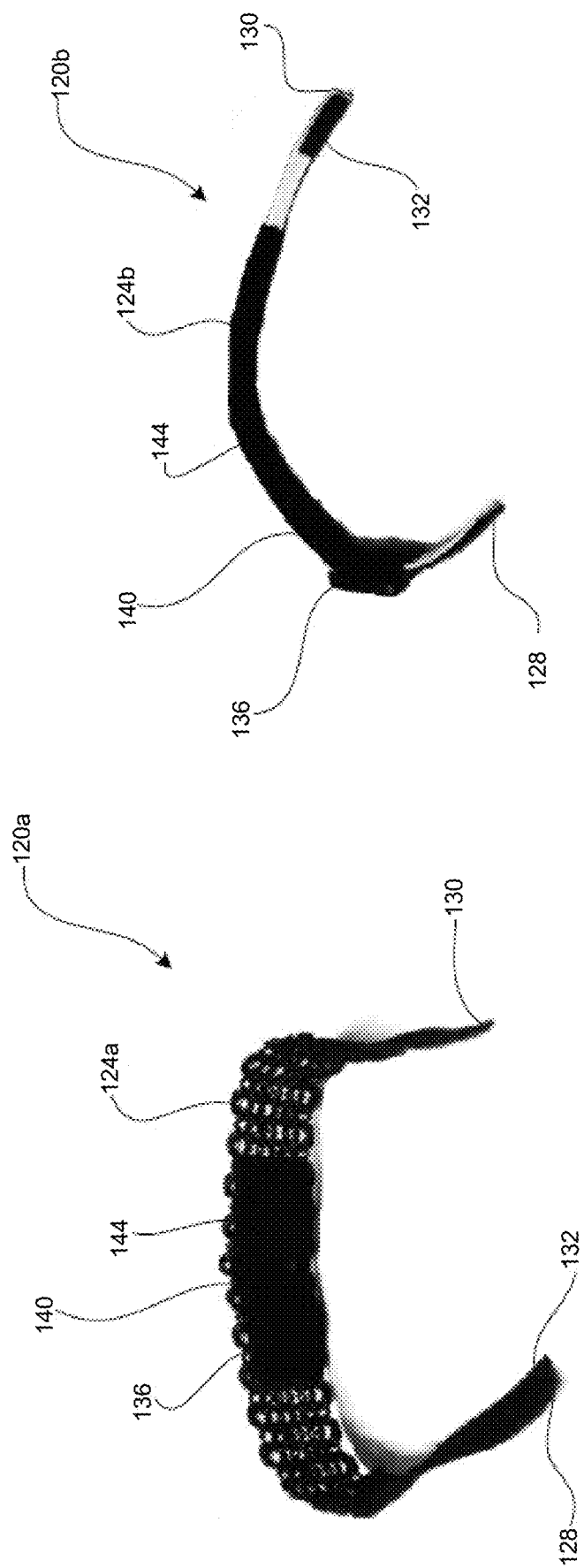

SYSTEM AND METHOD FOR MONITORING DIETARY ACTIVITY

CLAIM OF PRIORITY

This application claims priority to U.S. Provisional Application Ser. No. 62/637,800 entitled "Wearable Neckband Dietary Activity Monitoring Apparatus and Method" filed Mar. 2, 2018, the disclosure of which is incorporated herein by reference in its entirety.

TECHNICAL FIELD

This disclosure relates generally to dietary monitoring and, more particularly, to a wearable system and method for monitoring and classifying dietary activity.

BACKGROUND

Unless otherwise indicated herein, the materials described in this section are not prior art to the claims in this application and are not admitted to the prior art by inclusion in this section.

Known wearable dietary activity monitoring systems have drawn increasing amounts of attention as the systems can track an individual daily intake, the food quantities, related calories, and nutrient data when diet tracking is active. The wearable dietary activity monitoring systems include: (a) image/camera based, (b) wrist-worn, (c) neck-worn, and (d) ear-bud based systems.

Image/camera based systems analyze photos of the food being consumed by the individual and aim to detect the number of calories consumed automatically. However, image/camera based systems are unable to confirm if the individual fully or partially consumed the food without manual feedback.

In another example, wristband based systems focus on the gesture and hand movement of the individual to detect eating/drinking activities. Again, such systems are unable to confirm if the individual fully or partially consumed the food, and are therefore highly inaccurate without manual feedback, e.g. self-reporting food consumption. On the other hand, throat-worn and ear-bud based systems are based on jaw muscle movement and sound activities detection. However, conventional systems cannot accurately monitor the amount of food ingested nor the calories consumed.

In general, head-worn based systems comprise either a stethoscope or a vibration sensor mounted within a housing. The stethoscope is capable of capturing breathing sounds, but is incapable in detecting high frequency characteristics of ingestion sounds. As such, the accuracy of stethoscope-based systems is low. Conventional vibration sensor-based systems have low sensitivity and may generate signals when the user moves. As such, the recorded vibrations are inaccurate and cannot be used to accurately classify ingestion activities.

Therefore, a wearable dietary activity monitoring system capable of accurately classifying chewing and swallowing sounds and monitoring food intake and calories would be beneficial.

SUMMARY

In one embodiment, a system for monitoring dietary activity of a user includes a wearable device having at least one audio input unit configured to record an audio sample corresponding to audio from a user's neck. The system further includes a processor configured to execute programmed instructions stored in a memory to obtain an audio sample from the audio input unit of a wearable device, determine segmental feature values of a set of selected features from the audio sample by extracting short-term features in the set of selected features from the audio sample and determining the segmental feature values of the set of selected features from the extracted short-term features. The processor is further configured to, using a classifier, classify a dietary activity based on the determined segmental feature values of the audio sample and generate an output corresponding to the classified dietary activity.

In some embodiments, the audio input unit includes one or more of an electret condenser microphone, a silicon microphone, a microelectromechanical system (MEMS) microphone, a dynamic microphone, a microphone array, and a vibration sensor.

The system includes an external device comprising the processor and the memory in some embodiments, and the wearable device further comprises a communication module. The processor is further configured to obtain the audio sample via wireless communication with the communication module.

In another embodiment, the processor is arranged in the wearable device.

In yet another embodiment, the wearable device is a neckband configured to be worn around the user's neck.

In further embodiments, the set of selected features and classifier parameters for the classifier stored in the memory are determined in a machine-learning training process.

In one embodiment of the system the classifier is one of a random forest, a gaussian mixture model, a linear discriminant analysis, a Naive Bayes, a decision tree, and a k-nearest neighbor classifier. The determining of the segmental feature values may further include segmenting the extracted short-term features into segments of a predetermined duration and applying statistical functions to the extracted short-term features in each segment.

In some embodiments, the short-term features include one or more of: at least one MFCC coefficient, a delta of at least one MFCC coefficient, a delta-delta of at least one MFCC coefficient, energy entropy, short-term energy, zero crossing rate, spectral flux, spectral crest, spectral skewness, spectral centroid, spectral slope, spectral decrease, spectral spread, spectral rolloff, and spectral flatness. The statistical functions may include one or more of mean, median, standard deviation, skewness, kurtosis, maximum, and minimum.

One embodiment of the system further includes an output device configured to generate a perceptible output, wherein the processor is configured to communicate with the output device to generate the output as the perceptible output.

In another embodiment, the generating of the output includes storing the output in the memory.

In some embodiments, the processor is further configured, before determining the segmental feature values of the set of selected features, to detect whether activity occurs in each frame of the audio sample by comparing an energy of the frame with a predetermined energy threshold.

In another embodiment, a method of monitoring dietary activity comprises: obtaining, with a processor, an audio sample from an audio input unit of a wearable device, the audio sample corresponding to audio from a user's neck; determining, with the processor, segmental feature values of a set of selected features from the audio sample, the determining of the segmental feature values comprising: extracting short-term features in the set of selected features from the audio sample; and determining the segmental feature values of the set of selected features from the extracted short-term features; classifying, with the processor using a classifier, a dietary activity based on the determined segmental feature values of the audio sample; and generating an output corresponding to the classified dietary activity.

In some embodiments of the method, the audio input unit includes one or more of an electret condenser microphone, a silicon microphone, a microelectromechanical system (MEMS) microphone, a dynamic microphone, a microphone array, and a vibration sensor.

In another embodiment, the obtaining of the audio sample includes obtaining the audio sample by wireless communication via a communication module of the wearable device, and the processor is arranged in an external device.

In a further embodiment, the processor is mounted in the wearable device.

In some embodiments of the method, the wearable device is a neckband.

The method may be performed such that the set of selected features and classifier parameters for the classifier are determined in a machine-learning training process.

The classifier of the method may be one of a random forest, a gaussian mixture model, a linear discriminant analysis, a Naive Bayes, a decision tree, and a k-nearest neighbor classifier. The determining of the segmental feature may include segmenting the extracted short-term features into segments of a predetermined duration and applying statistical functions to the extracted short-term features in each segment. The short-term features may include one or more of: at least one MFCC coefficient, a delta of at least one MFCC coefficient, a delta-delta of at least one MFCC coefficient, energy entropy, short-term energy, zero crossing rate, spectral flux, spectral crest, spectral skewness, spectral centroid, spectral slope, spectral decrease, spectral spread, spectral rolloff, and spectral flatness. The statistical functions may include one or more of mean, median, standard deviation, skewness, kurtosis, maximum, and minimum.

In another embodiment of the method, the generating of the output includes generating a perceptible output via an output device.

A wearable neckband according to the disclosure includes at least one audio input unit comprising one or more of an electret condenser microphone, a silicon microphone, a microelectromechanical system (MEMS) microphone, a dynamic microphone, a microphone array, and a vibration sensor configured to record an audio sample corresponding to audio from a user's neck, a communication module configured to wirelessly transmit the recorded audio sample to an external device, an energy storage unit configured to store electrical power for operation of the at least one audio input unit and the communication module, and a housing in which the at least one audio input unit, the communication module, and the energy storage unit are arranged, the housing being elastically deformable and including a fastening arrangement at each end of the housing.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein:

FIG. 3 is a simplified perspective view of an exemplary wearable neckband dietary activity monitoring apparatus according to a described embodiment of the disclosure.

FIG. 4 is a simplified perspective view of an exemplary wearable neckband dietary activity monitoring apparatus according to a described embodiment of the disclosure.

FIG. 7b is a schematic block diagram of the dietary activity monitoring system of FIG. 7a.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one skilled in the art to which this document pertains.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The terms "comprising," "including," "having," and the like, as used with respect to embodiments of the disclosure, are synonymous. As used herein, the term "approximately" refers to values that are within ±20% of the reference value.

Figure 1:
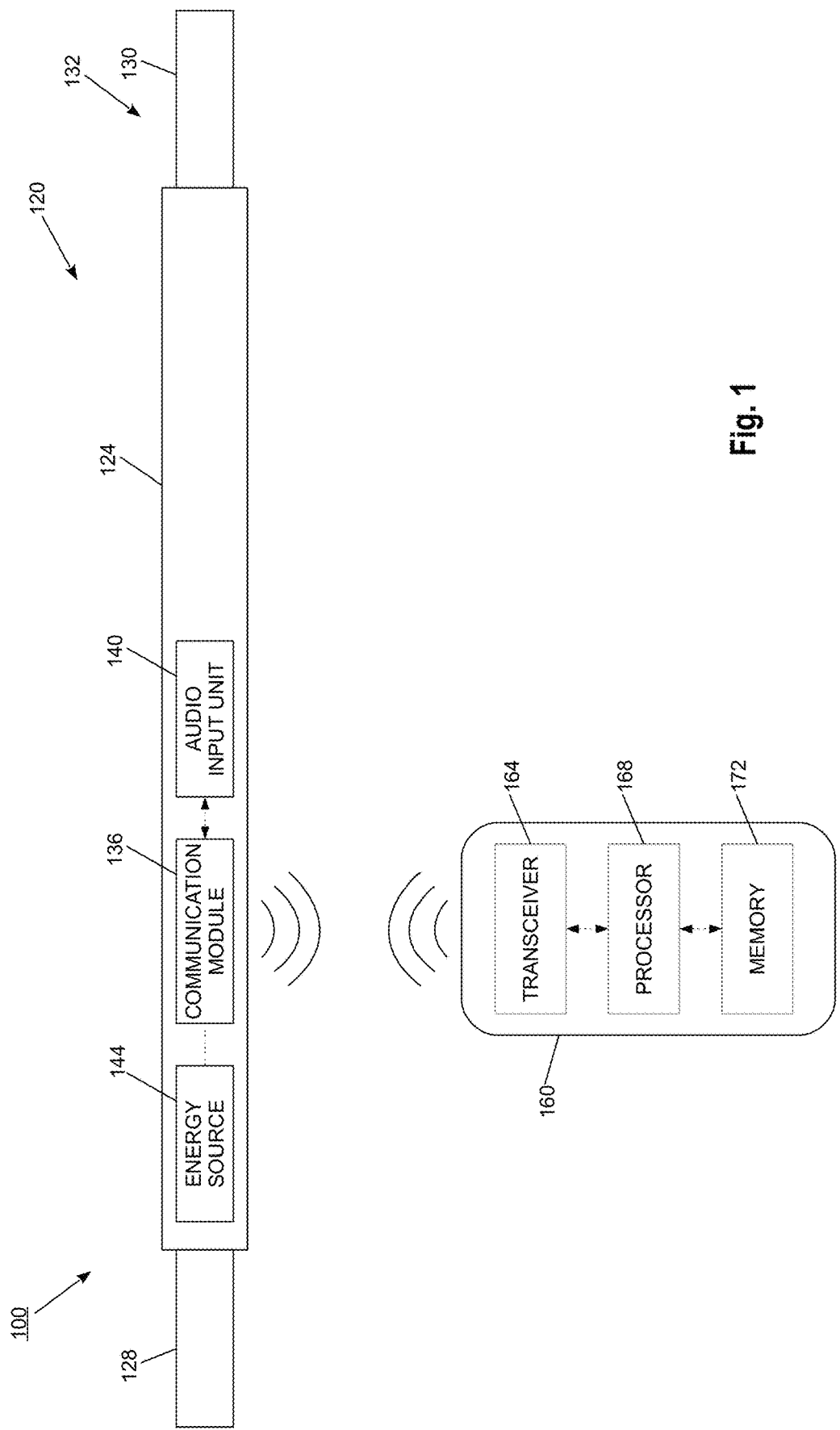
FIG. 1 is a schematic illustration of a dietary activity monitoring system in which a wearable device communicates with an external device.

FIG. 1 illustrates a schematic illustration of a dietary activity monitoring system 100 having a wearable device which, in the illustrated embodiment, is a neckband monitoring apparatus 120 configured to monitor and track a user's dietary intake. As described herein, the monitoring apparatus 120 is configured to be worn around a human's neck to monitor human food and drink consumption. In some embodiments, the monitoring apparatus 120 may be worn at a different location on the user's body where chewing and swallowing noises can be sensed, for example on the jaw, head, mouth, cheek, chest, or other desired location. In addition, the reader should appreciate that in some embodiments the wearable device may be configured to be worn on an animal, for example around an animal's neck to track the animal's food and drink consumption. Additionally, while FIG. 1 depicts the monitoring apparatus 120 as a neckband, the reader should appreciate that the monitoring apparatus may be configured as another wearable device, such as, for example a necklace, a pendant, or the like.

The monitoring apparatus 120 comprises a housing 124 having first and second ends 128, 130. In some embodiments, the housing 124 may be a single, continuous body housing, while in other embodiments the housing 124 may include a multi-layered continuous body housing, multiple joined sections attached together to form a continuous body housing, or multiple housing parts that form a discontinuous housing. The housing 124 is formed from an elastically stretchable material that is capable of forming to the neck of the individual and may be, in some embodiments, an elastic strap covered in velvet or another comfortable and wearable fabric. In one embodiment, the housing 124 may be formed of a biomaterial or a biocompatible material. In some embodiments, the housing 124 is formed from a shape forming polymer that is elastic, stretchable, and configured to return to its original shape and length. In a further embodiment, the housing 124 is made from a material that is bendable and foldable when the monitoring apparatus 120 is placed so that the monitoring apparatus 120 can be easily stored when it is not being worn by the user.

A locking or fastening assembly 132 is incorporated to the ends 128, 130 of the housing 124. As illustrated, the locking or fastening assembly 132 is configured as a hook and loop type fastener system (e.g. Velcro®) in which one end, for example end 128, has the hook portion and the other end, for example end 130, has the loop portion. In other embodiments, the locking or fastening assembly 132 is another desired fastening arrangement, for example a magnetic connector, a button fastener, laces, a clasp such as a lobster clasp, a spring ring, a bayonet clasp, or a barrel clasp, or the like. In another embodiment, the locking or fastening assembly 132 is formed as a permanent connection between the ends 128, 130, such that user dons and doffs the monitoring apparatus 120 by elastically stretching the monitoring apparatus 120 so as to fit the monitoring apparatus 120 over the user's head.

A communication module 136, an audio input unit 140, and an energy source 144 are mounted to or within the housing 124. Other computer implemented modules such as: computer readable medium, for example a memory 152 (e.g. FIG. 2); an input and/or output interface 156 (e.g. FIG. 2), for example a display, a touchscreen, a track pad, a switch, a button, an indicator, and/or one or more LEDs; a digital signal processing unit (DSP) 148 (e.g. FIG. 2); and any other desired modules may be incorporated into or onto the housing 124.

The communication module 136 is configured to communicate with one or more external devices 160, for example machine devices, networks, servers, and/or other devices, to transmit parameters and data collected by the monitoring apparatus 120. As used herein, a smart device refers to a cellular telephone or smartphone, a tablet, a smart watch, or the like. The communication module 136 may be configured for any suitable wireless communication protocol, such as, for example Bluetooth®, near-field-communication, Internet-data-communication, wireless telephone networks, Wi-Fi®, ZigBee®, Z-Wave®, Thread®, an ultrasound protocol, and the like. In certain embodiments, the communication module 136 may be configured for wired data transmission via, for example, a USB, Ethernet, or another suitable wired data connection protocol. As illustrated, the communication module 136 is a Bluetooth® transmitter or transceiver.

The machine devices may be one or more of: cellular devices such as smartphones; portable devices; wearable devices such as watches, glasses, or goggles; laptops; desktops, tablets; entertainment systems, for example televisions; voice-activated devices with or without a display, for example digital personal assistants (e.g. Alexa®, Google Assistant®, Siri®, Cortana®, etc.), and any suitable machine devices capable to receive, store, and/or display information collected by the monitoring apparatus 120. The networks can be one or more communication networks of any suitable type in any combination, including wireless networks, wired networks, local area networks, wide area networks, cellular data networks, the Internet, cloud networks, and so forth. The servers may be implemented by any configuration or of one more computer machines, such as remote server computers, or the like.

In the illustrated embodiment, the audio input unit 140 includes a single electret condenser microphone (ECM) capable of capturing swallowing and chewing sound activities during food intake events. In other embodiments, the audio input unit 140 may include one or more of silicon microphones, microelectromechanical system (MEMS) microphones, dynamic microphones, microphone arrays, vibration sensors (e.g. piezoelectric sensors), and the like. In further embodiments, the audio input unit 140 may include a plurality of electret microphones, a plurality of other types of audio sensors, or a combination of the two. In some embodiments, the audio input unit 140, or a separate input unit, may include a motion sensor, accelerometer, camera, and/or any other desired input unit.

The energy source 144 may be, for example, a rechargeable battery. In one particular embodiment, the energy source is a 100 mAh Li-based battery. The energy source 144 may be charged by, for example, a wired connection (e.g. USB® or a dedicated AC or DC power supply), inductive charging (e.g. Qi charging), RF charging, an energy harvesting system, or the like.

The dietary activity monitoring system 100 further includes a processor 168 operably connected to a memory 172. In the embodiment of FIG. 1, the processor 168 and memory 172 are arranged in the external device 160, which includes a transceiver 164 that communicates with the communication module 136 of the monitoring apparatus 120. In another embodiment, illustrated schematically in FIG. 2, the processor 168 and memory 172 are integrated in or on the housing 124 of the monitoring apparatus 120. In some embodiments, the processor 168 may be integrated in the communication module 136 and/or the audio input unit 140. In further embodiments, the monitoring apparatus 120 and the external device 160 each have processors, which can jointly or separately perform data processing on the data collected by the audio input unit 140.

It will be recognized by those of ordinary skill in the art that a "processor" includes any hardware system, hardware mechanism or hardware component that processes data, signals or other information. The processor 168 may include a system with a central processing unit, multiple processing units, dedicated circuitry for achieving functionality, or other systems.

The memory 172 may be of any type of device capable of storing information accessible by the processor 168, such as write-capable memories, read-only memories, a memory card, ROM, RAM, hard drives, discs, flash memory, or other computer-readable medium. The memory 172 is configured to store program instructions that, when executed by the processor 168, enable the processor 168 to perform one or more of ingestion activity detection, feature extraction, and classification, as described in further detail below.

In particular, the memory 172 is configured to store program instructions corresponding to at least one machine learning model, in particular to an ingestion classification model and classification parameters thereof. The processor 144 is configured to utilize the ingestion classification model to extract features from the audio signal or signals and to classify the consumption of the user based on the audio signals. As used herein, the term "machine learning model" refers to a system or set of program instructions and/or data configured to implement an algorithm or mathematical model that predicts and provides a desired output based on a given input. It will be appreciated that parameters of a machine learning model are not explicitly programmed or the machine learning model is not necessarily designed to follow particular rules in order to provide the desired output for a given input. Instead, the machine learning model is provided with a corpus of training data from which the processor identifies or "learns" patterns and statistical relationships or structures in the data, which are generalized to make predictions with respect to new data inputs. The classification parameters include a plurality of values for parameters of the ingestion activity classification model which were learned during a training process.

FIGS. 3 and 4 illustrate simplified perspective views of exemplary wearable neckband activity monitoring apparatuses 120a, 120b. In the embodiment of FIG. 3, the housing 124a includes a woven elastic fabric. The communication module 136, audio input unit 140, and energy source 144 are attached to the woven elastic fabric and enclosed in an elastic fabric so as to protect the communication module 136, audio input unit 140, and energy source 144.

In the embodiment of FIG. 4, the housing 124b includes an fabric tube covering the elastic band. The fabric tube may be, for example, velvet, cloth, or another comfortable fabric. The audio input unit 140 and energy source 144 are arranged in the fabric tube, while the communication module 136 is mounted to the exterior of the elastic tube in the embodiment of FIG. 4.

System Training

Figure 2:
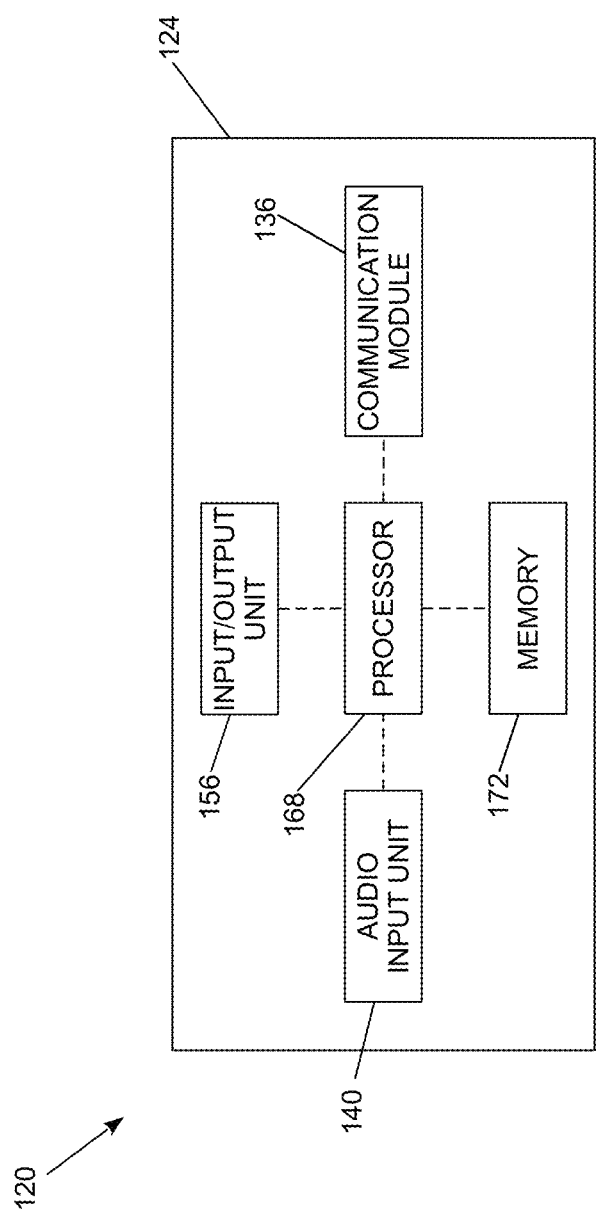
FIG. 2 is a schematic illustration of the dietary activity monitoring system in which the wearable device includes a processor and memory.
Figure 5:
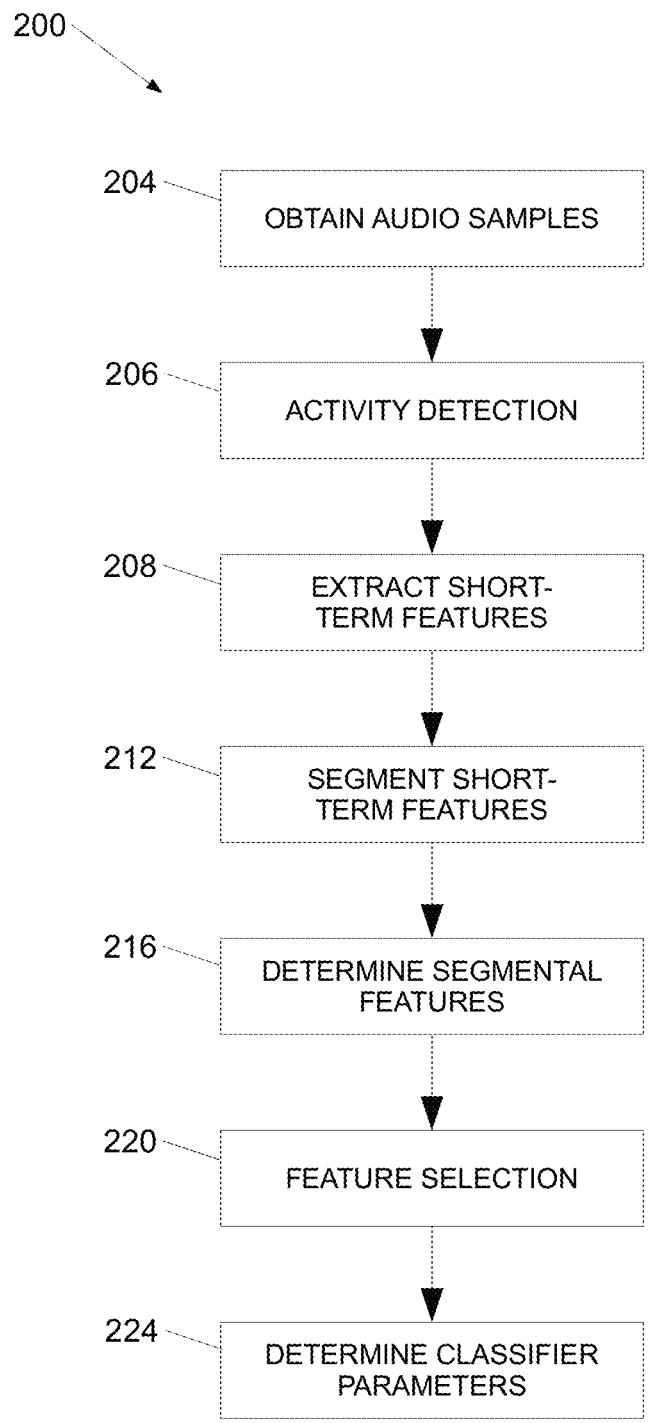
FIG. 5 is a process diagram of a method of training and/or calibrating the dietary activity monitoring system of FIG. 1.
Figure 6:
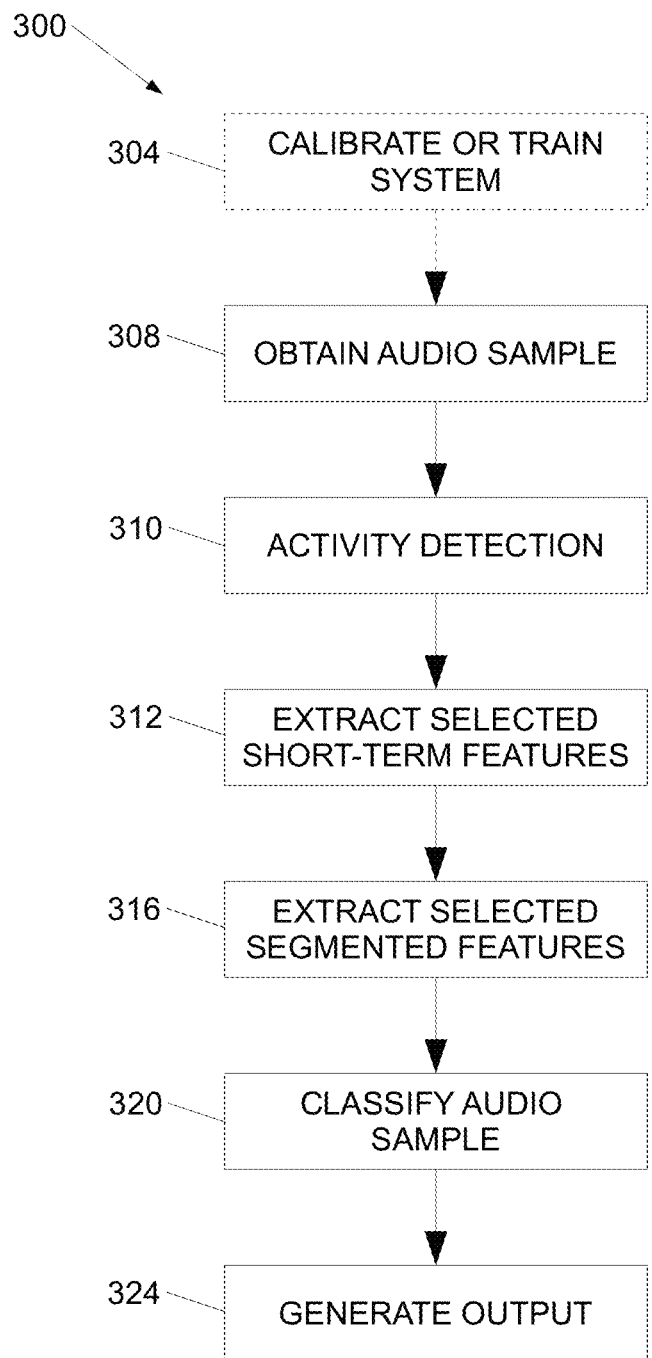
FIG. 6 is a process diagram of a method of classifying a dietary activity using the dietary activity monitoring system of FIG. 1.

FIG. 5 illustrates a machine learning process 200 for training a machine-learning ingestion classification system such as the dietary activity monitoring system 100 of FIGS. 1 and 2 to classify the ingestion of a user. In the description of the methods, statements that a method is performing some task or function refers to a controller or general purpose processor executing programmed instructions stored in non-transitory computer readable storage media operatively connected to the controller or processor to manipulate data or to operate one or more components in the dietary activity monitoring system 100 to perform the task or function. Particularly, the processor 168 of the dietary activity monitoring system 100 described above may be such a controller or processor. Alternatively, the controller or processor may be implemented with more than one processor and associated circuitry and components, each of which is configured to form one or more tasks or functions described herein. It will be appreciated that some or all of the operations the method can also be performed by a remote server or cloud processing infrastructure. Additionally, the steps of the methods may be performed in any feasible chronological order, regardless of the order shown in the figures or the order in which the steps are described.

The process 200 begins by obtaining audio samples (block 204). In one embodiment, the audio samples are sensed by a single audio sensor, for example the audio input unit or electret microphone 140. The processor communicates with the one or more audio sensors to receive a time series of acoustic values corresponding to the detected audio. The audio samples may include a dataset of a variety of known swallowing and speaking activities from a plurality of subjects that are detected by the audio input unit 140 and stored in a memory associated with the processor, for example the memory 172.

In some embodiments, the extraction of the audio features begins with an activity detection process (block 206.) The audio signal is divided into frames of, for example, between approximately 10 ms and approximately 100 ms, or, in another embodiment, approximately 40 ms. The processor then determines the audio energy of the frame (i.e. the summation of the square power of the signal) according to the following equation:

$$\text{Energy} = \sum_t |\text{signal}(t)|^2 / \text{length}(\text{signal}) |$$

If the energy is below a predetermined threshold, the audio frame is discarded as containing no relevant dietary activity. If the energy is above the predetermined threshold, it is assumed that there is some activity detected in the frame, and the audio sample is retained for further processing.

When the method 200 proceeds with extracting features from the audio samples (block 208), the processor begins by separating the audio samples into short-term frames. In one embodiment, the frames are between approximately 5 ms and approximately 500 ms. In another embodiment, the frames are between approximately 20 ms and approximately 80 ms. In one particular embodiment, the frames are approximately or exactly 40 ms. The frames may be non-overlapping in one embodiment. In another embodiment, the frames may overlap by between approximately 25% and approximately 90%. In one particular embodiment, the frames overlap by approximately or exactly 75%.

The feature extraction continues with determining short-term features for each frame. Table 1 illustrates a list of short-term features that may be extracted in one embodiment of the process 200.

TABLE 1

Short-Term Feature Ensemble

| Index | Feature name |
| --- | --- |
| 1-21 | Static MFCC |
| 22-63 | Delta & acceleration |
| 64 | Energy entropy |
| 65 | Short-term Energy |
| 66 | Zero crossing rate |
| 67 | Spectral flux |

TABLE 1-continued

Short-Term Feature Ensemble

| Index | Feature name |
|---|---|
| 68 | Spectral crest |
| 69 | Spectral skewness |
| 70 | Spectral centroid |
| 71 | Spectral slope |
| 72 | Spectral decrease |
| 73 | Spectral spread |
| 74-75 | Spectal rolloff (25%, 50%) |
| 76 | Spectral flatness |

The mel-frequency cepstral coefficients (MFCC) and their differential (also referred to as "delta" or "d") and acceleration (also referred to as "delta-delta" or "dd") coefficients are coefficients that are commonly used in the art to enable automated frequency detection to interpret frequency differences more like the human ear. In one embodiment, the MFCC's are calculated with 30 filter banks, and the static coefficients for the lower 21 filter banks, and their associated delta and acceleration coefficients, are retained, though the reader should appreciate that other numbers of filter banks may be calculated and retained in other embodiments.

Figure 12:
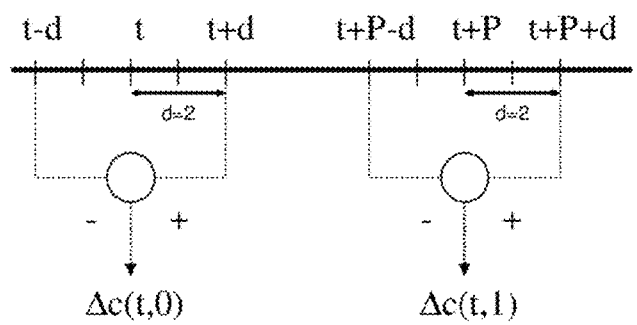
FIG. 12 is an illustration depicting of one form of computing shifted delta cepstral coefficients.

With the 63 MFCC coefficients and the spectral, waveform, and energy based features listed in Table 1, each frame includes a 76 dimensional feature vector. The reader should appreciate that in other embodiments, other features and/or fewer features may be extracted from the frames. Additionally, in some embodiments, shifted delta cepstral (SDC) coefficients are used instead of delta coefficients. The shifted delta coefficients are generalized version of delta coefficients and are extracted by subtracting the feature vectors (MFCCs) from a longer duration time-span (d). FIG. 12 illustrates the computation of SDC features $\Delta c$. The parameter d determines the spread over which deltas are calculated, and the parameter P determines the gaps between successive delta computations. For unshifted delta coefficients, d=1 and P=1 is used, whereas for SDC, larger values of d and P are used. In one embodiment, the SDC's for the diet monitoring system may be d=2 and P=2.

The process 200 continues by partitioning the features into segments with a fixed length in time (block 212). In segmenting the features, the extracted feature vectors are grouped together over the segment length to enable statistical functions to be performed for each segment. In some embodiments, the segments fully overlap, i.e. the segments have an offset of only one frame from adjacent segments. In other embodiments, the segments may only partially overlap, such that each segment is shifted by 5, 10, 25, or 50 frames, or by any other desired number of frames, from the temporally adjacent segment. In further embodiments, the segments may have no overlap with one another.

The segments may have length of, for example, between 0.1 second and 60 seconds. In one embodiment, the segments have length of between 1 second and 10 seconds. In some embodiments, the features are partitioned into approximately or exactly 3 second segments. In other embodiments, the features may be partitioned into different segment lengths depending on the statistical functions applied to the segments, the accuracy desired, computational resources available, and other parameters. Furthermore, in some embodiments, the processor analyzes different segment lengths for the features to investigate the optimum time window for the particular ingestion determination. The optimum time window may be based on the features in the audio signal and/or the features of the individual or task being analyzed.

Next, the process 200 proceeds with the processor applying statistical functions to determined segmental features for each segment (block 216). Table 2 illustrates the statistical functions for one exemplary embodiment. The reader should appreciate, however, that other functions and/or fewer functions may be applied to the segmental features.

TABLE 2

Statistical Functions for Segmental Features

| Averages | Moments | Extremes |
|---|---|---|
| Mean | Standard Deviation | Maximum |
| Median | Skewness | Minimum |
|  | Kurtosis |  |

The processor may be configured to determine every functional of every segment as the determined segmental functions. Alternatively, the processor may be configured to determine a limited number of segmental functions to reduce computational resources necessary for the determination of the segmental functions.

Using the seven statistical functions of Table 2 on the 76 dimensional feature vector of produced using the features of Table 1 results in 532 dimensional segmented feature vectors. After the determination of the segmental features, a feature selection step is performed to reduce the number of feature to a selected feature set (block 220). In one embodiment, the features are selected according to the ReliefF method. In other embodiments, other known feature selection methods may be used to select the feature set of coefficients most relevant to the determination of the ingestion classification. In one embodiment, the ReliefF method is used to select a feature set of approximately or exactly 76 features, though other numbers of features may be selected in other embodiments.

The process concludes by classifying the selected features (block 224). In one embodiment, the processor is configured to implement a random forest classifier on the selected features. The random forest classifier may be generated using approximately or exactly 76 bags per tree and use a classification decision tree method. Bagging is an ensemble learning method that can be used for any machine learning (ML) algorithm. In the illustrated embodiment, the ML algorithm is random forest, and the ensemble learning method is bagging. In particular, the training data is randomly sampled with replacement and the classification algorithm (e.g. random forest) is run in each sub-set, or bag, of samples, and the bags are later combined by averaging the results from each sub-set.

In another embodiment, the classifier may be determined using a Gaussian mixture model (GMM) having, for example, approximately 16 mixture components and approximately 50 iterations. In a further embodiment, the classifier may be determined using a linear discriminant analysis with a linear kernel and Bayesian optimization. In yet another embodiment, the classifier may be determined using a Naive Bayes classifier having a normal distribution kernel and a maximum objective evaluation of approximately 30. In some embodiments, the processor determines a decision tree classifier with a maximum grid division of 10. In a further embodiment, the classifier is determined using a k-nearest neighbor classifier having approximately 5 neighbors and using a kd-tree neighbor search method. The reader should appreciate that other classifier models may be used in other embodiments as well.

In some embodiments, the training process 200 is performed on a computer or server, and the resulting features and classifier are stored in the memory 172 of the dietary activity monitoring system 100. In such embodiments, the dietary activity monitoring system 100 may be easily adapted to a variety of different uses with reduced outlay and installation cost since the results of the training process can be pre-installed in the dietary activity monitoring system 100.

In another embodiment, the training process is performed as a system calibration when the dietary activity monitoring system 100 is first used. The training data may then be stored in the memory 172 for subsequent use. In addition, the training process may be based on both pre-installed data and training data obtained during a calibration step. The dietary activity monitoring system 100 machine learning algorithm can therefore be tailored to an individual user while also including sufficient data to produce accurate results. In such embodiments, a high degree of accuracy is obtainable since the features and classification parameters are based on the specific characteristics of the user that is to be using the dietary activity monitoring system 100.

Ingestion Activity Detection and Monitoring

FIG. 4 illustrates a flow chart of a process 300 for monitoring dietary activity. The process 300 refers to a processor, for example the processor 168 executing programmed instructions stored in a memory, for example memory 172, to perform the functions described below to classify a dietary activity. In the description of the methods, statements that a method is performing some task or function refers to a controller or general purpose processor executing programmed instructions stored in non-transitory computer readable storage media operatively connected to the controller or processor to manipulate data or to operate one or more components in the dietary activity monitoring system 100 to perform the task or function. Particularly, the processor 168 of the dietary activity monitoring systems 100 described above may be such a controller or processor. Alternatively, the controller or processor may be implemented with more than one processor and associated circuitry and components, each of which is configured to form one or more tasks or functions described herein. It will be appreciated that some or all of the operations the method can also be performed by a remote server or cloud processing infrastructure. Additionally, the steps of the methods may be performed in any feasible chronological order, regardless of the order shown in the figures or the order in which the steps are described. By way of example, in some embodiments, the process 300 may be performed by the external device 160, while in other embodiments the process 300 may be performed by the wearable neckband monitoring apparatus 120.

In some embodiments, the process 300 begins by calibrating or training the system (block 304). The training may, for example, be performed using the process 200 of FIG. 5. The selected short-term features, segmental features, and/or classifier parameters, for example the random forest, from the calibration or training of the system are stored in the memory, e.g. memory 172, associated with the processor 168. In other embodiments, the system may be pre-programmed with the selected short-term features, the selected set of segmental features, and/or the classification algorithm such that some or all of the calibration or training of the machine-learning dietary classification system is not necessary.

The process then proceeds with the processor obtaining an audio sample (block 308) using an audio input unit, for example an electret microphone. In one embodiment, the audio sample is sensed by a single audio sensor, for example the audio input unit 140 of the wearable monitoring apparatus 120. In another embodiment, the audio sample is sensed by a plurality of audio sensors of the audio input unit or of multiple audio input units. The processor communicates with the one or more audio sensors to receive a time series of acoustic values corresponding to the audio detected by the wearable monitoring apparatus 120. The processor obtains the sensed audio sample from the audio sensor(s) via direct connection or via communication over a wired or wireless network. The obtaining of the audio sample by the processor may occur continuously while the wearable monitoring apparatus 120 is powered on, the processor may be configured to obtain a plurality of audio samples in batches. In one particular embodiment, the audio samples are obtained in real time with three second buffers. In other embodiments, the audio data may be stored in a memory, for example memory 172, and the processor may obtain the stored audio data when physically connected to the audio input unit and/or when prompted by a user, for example in a "syncing" process.

Since the audio input unit may be continuously collecting audio data, in some embodiments, the extraction of the audio features begins with an activity detection process (block 310.) Similar to the activity detection process (block 206) described above, the processor is configured to divide the audio sample into frames of, for example, between approximately 10 ms and approximately 100 ms, or, in another embodiment, approximately 40 ms. The processor then determines the audio energy of the frame and, if the energy is below a predetermined threshold, the audio frame is discarded as containing no relevant dietary activity. If the energy is above the predetermined threshold, it is assumed that there is some activity detected in the frame, and the audio sample is retained for further processing. The activity detection process reduces the computational resources used by the system 100, since audio samples during which no activity occurs are discarded with minimal processing.

Next, the processor determines the selected short-term features from the audio sample (block 312). The short-term feature extraction is performed in a similar manner as in the short-term feature extraction step 208 described above, with the exception that only the short-term features selected during the calibration and training process, for example in the step 304 or the training process 200 described above, are extracted. The features frames may have similar length as the feature frames used during the feature extraction step described above, or the feature frames may have different lengths. In one embodiment, the frames are between approximately 5 ms and approximately 500 ms. In another embodiment, the frames are between approximately 20 ms and approximately 80 ms. In one particular embodiment, the frames are approximately or exactly 40 ms. The frames may be non-overlapping in one embodiment. In another embodiment, the frames may overlap by between approximately 25% and approximately 90%. In one particular embodiment, the frames overlap by approximately or exactly 75%.

In contrast to the training process 200 described above, the process 300 for classifying the dietary activity is limited in the number of short-term features determined. In particular, only the short-term features needed to calculate the segmental features of the selected set of features are determined in the process 300. The reader should appreciate, however, that any desired number of short-term features may be used depending on the desired accuracy and computational resources available. Additionally, the selected short-term features may vary based on the data received from executing the machine learning models. The selected short-term features may be those short-term features that provide the greatest amount of information related to the classification of the ingestion activity.

The process continues with segmenting and extracting the segmental features from the extracted short-term features (block 316). Again, the processor is configured to segment the extracted short-term feature vectors into groups of a predetermined time length to enable statistical functions to be performed for each segment. In some embodiments, the segments fully overlap, i.e. the segments have an offset of only one frame from adjacent segments. In other embodiments, the segments may only partially overlap, such that each segment is shifted by 5, 10, 25, or 50 frames, or by any other desired number of frames, from the temporally adjacent segment. In further embodiments, the segments may have no overlap with one another.

The segments may have length of, for example, between 0.1 second and 60 seconds. In one embodiment, the segments have length of between 1 second and 10 seconds. In some embodiments, the features are partitioned into approximately or exactly 3 second segments. In other embodiments, the features may be partitioned into different segment lengths depending on the statistical functions applied to the segments, the accuracy desired, computational resources available, and other parameters. Furthermore, in some embodiments, the processor analyzes different segment lengths for the features to investigate the optimum time window for the particular ingestion determination. The optimum time window may be based on the features in the audio signal and/or the features of the individual or task being analyzed.

The segmental features are then determined from the segments by applying statistical functions on the segmental feature vectors, in a similar manner as in step 216 above. However, only those segmental features that are stored as the selected set of features are determined, thereby limiting the computational resources necessary for the computation.

Finally, the process concludes by classifying the audio sample (block 320). As discussed above, the classifier may be developed using a machine learning model such as the machine-learning training process of FIG. 5. In one embodiment, the classifier is a random forest classifier, though other classifiers such as Gaussian mixture model, linear discriminant analysis, Naive Bayes, decision tree, and/or k-nearest neighbor classifiers may be used in other embodiments. The extracted selected segmented features are input into the classifier, which determines, based on the segmented features, an ingestion activity that is likely recorded in the recorded audio sample. The classifier output may be, in one embodiment, probability of a certain ingestion activity based on the recorded audio. In another embodiment, the classifier output may be a particular activity that is most likely.

The method 300 continues by generating an output based on the determination of occupancy (block 324). In some embodiments, the output is based on matching the audio signal to a known food or drink type and quantity stored in a database in the memory 172 or in a remote memory or server based on the results of the classifier. The output may, in one embodiment, be a perceptible output as to the ingestion activity detected using the classifier depicted on a user interface, for example a screen on the external device 160 or the wearable monitoring apparatus 120. The perceptible output may include an indication of the ingestion activity detected, and/or an estimated caloric quantity or nutritional facts (e.g. macronutrients and/or micronutrients, etc.) in the ingested food or drink. In other embodiments, the perceptible output may be an audible indicator, such as an audio alert specifying the ingestion activity detected and/or the estimated caloric quantity or nutritional facts in the activity.

In a further embodiment, the output is an electronic signal transmitted to another electronic device or stored in a memory or the memory 172. For example, the output may be an electronic signal output to the external device 160 or a different external device. In some embodiments, the output is stored in the memory 172 and, and multiple outputs are aggregated over a specified time period, for example one day. In another embodiment, the output is stored in the memory 172 and can be recalled by a user when desired so that the user can track his or her nutritional input over a specified time period.

The disclosed dietary activity monitoring system 100 provides a number of improvements to computer and nutritional or dietary activity tracking and monitoring technology by affording an efficient and cost-effective way to track dietary and nutritional activity. In one embodiment, the neckband monitoring apparatus 120 requires only readily available and inexpensive components, for example a microphone, in particular an electret microphone, a battery, and a transmitter, in particular a Bluetooth® transmitter. The dietary activity monitoring system 100 can therefore be produced inexpensively, thereby enabling dietary activity tracking at low cost, which is an improvement over conventional dietary activity tracking technology.

In addition, since the dietary activity monitoring system 100 detects nutritional activity automatically, the nutritional tracking is done with minimal user input. Since many conventional dietary and nutritional tracking systems require user input, the nutritional profile is frequently incomplete, as a user may forget or neglect to record some activities, or may stop tracking nutritional activities altogether due to the time required to input the activities. The automatically recording of nutritional and dietary activities of the disclosed dietary activity monitoring system 100 thereby provides a more complete nutritional record for the user. As such, the disclosed dietary activity monitoring system 100 is a further improvement on dietary tracking technology.

Moreover, in many conventional automated nutritional tracking systems, the systems are not capable of confirming the quantity of food or drink consumed by the user. Since the disclosed dietary activity monitoring system 100 detects nutritional activity based on chewing and swallowing sounds, the dietary activity monitoring system 100 can more accurately detect the quantity of food or drink consumed. Thus, for this additional reason, the dietary activity monitoring system 100 is a further improvement over conventional dietary tracking technology.

Other conventional nutritional tracking systems operated based on limited frequency or sensitivity. In particular, use of an electret microphone provides reduced sensitivity to contact with the user's skin as compared to a laminated piezoelectric plate microphone. Since sensitivity to a user's skin causes undesirable readings and distortion of sounds during movement of a user's head, the electret microphone provides improved audio signal capture. Furthermore, it is difficult or impossible to accurately capture swallowing signals using piezoelectric microphone sensors, and the disclosed electret sensor thereby provides improved audio detection. As such, the disclosed dietary activity monitoring system 100 is an improvement to conventional nutritional tracking systems since the dietary activity monitoring system 100 sensitively detects a wide range of frequencies, thereby affording improved accuracy over conventional systems.

Experimental Results

Figure 7A:
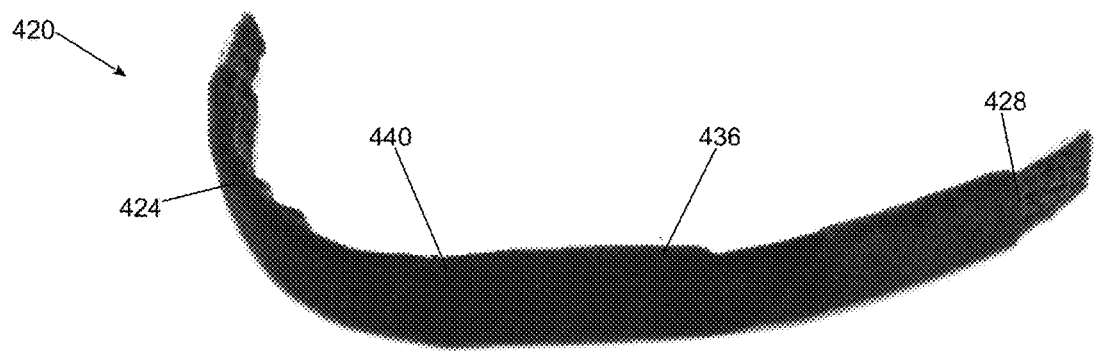
FIG. 7a is a perspective view of an experimental embodiment of a dietary activity monitoring system.
Figure 7B:
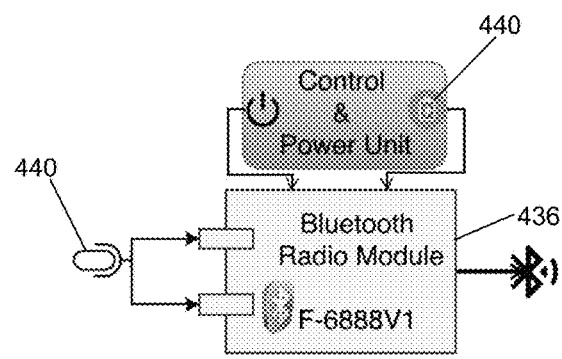

An experiment was performed using an embodiment of the dietary activity monitoring system 100. As illustrated in FIG. 7a, the experimental system includes a neckband 420 is designed using a housing 424 including an elastic band covered with a velvet fabric. The housing 424 further includes an adjustable hook and loop strap 428 on both ends. The fabric-based design is inexpensive to implement, and provides for the user's comfort to ensure that the user can comfortably wear the device throughout the day.

Figure 8A:
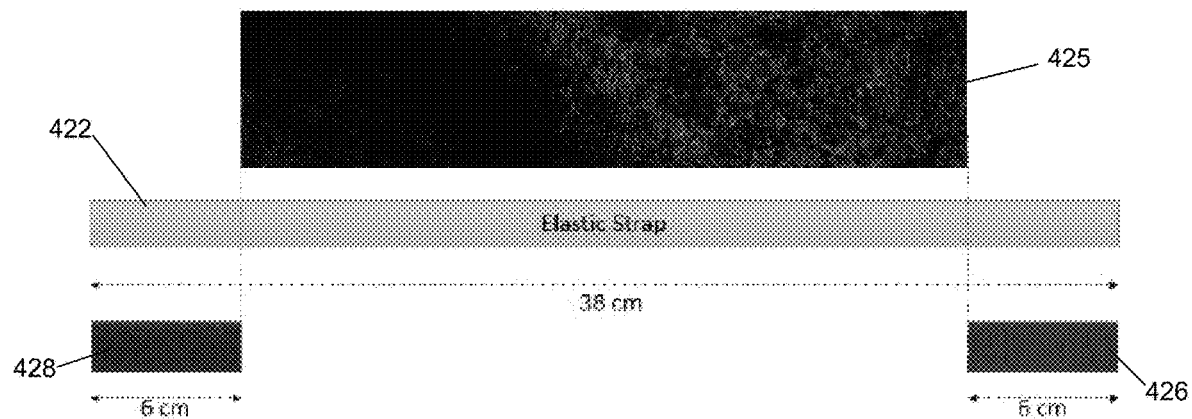
FIG. 8a is a schematic view of the experimental embodiment of FIG. 7a before any components are affixed to the elastic strap.

The exemplary embodiment of the neckband 420 was fabricated by first cutting an elastic strap to a desired length, as illustrated in FIG. 8a. In one embodiment, the elastic strap 422 was cut to a length of approximately 38 cm out of elastic that was capable of expanding to approximately 45 cm under strain. A velvet fabric 425 was cut to a length of approximately 26 cm, while hook and loop ends were cut to a length of approximately 6 cm for each end (i.e. a hook portion 426 at one end and a loop portion 428 at the opposite end).

Figure 8B:
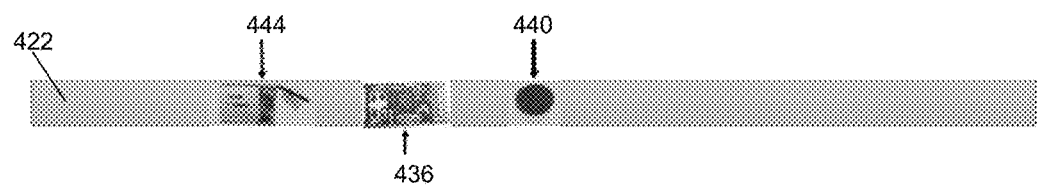
FIG. 8b is a schematic view of the elastic strap of FIG. 8a after the electret condenser microphone, Bluetooth® module, and battery are affixed to the elastic strap.

An electret microphone 440 was adhered to the elastic strap approximately or exactly at the center of the elastic strap using, for example, glue (FIG. 8b). The electret microphone 440 was wired to a Bluetooth® 4.0 module 436, which was a F-6888V1 Bluetooth 4.0 module powered by a rechargeable 100 mAh Lithium-ion battery 444 in the illustrated embodiment. The Bluetooth® module 436 and battery 444 were adhered to the elastic band inside the fabric neckband with at least 2 cm space between each element 440, 436, 444. The electret microphone may have, for example, a radius of 2.2 mm with a sensitivity range of ~44 dB to ~66 dB and a maximum current rating of 0.5 mA. A power button was attached and glued to the Bluetooth module so as to enable the user to power the neckband on and off.

Figure 8C:
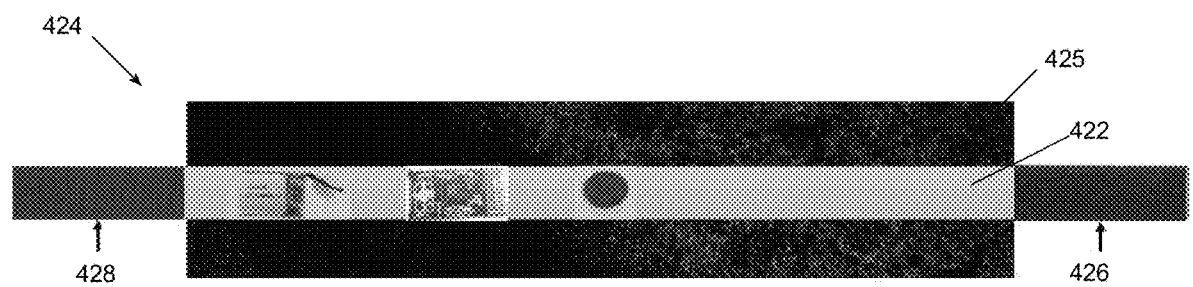
FIG. 8c is a schematic view of the housing components affixed to the elastic strap of FIG. 8b.

The hook and loop ends 426, 428 were attached to the elastic strap 422, and the velvet fabric 435 was wrapped over the central portion of the elastic strap 422 adjacent to the hook and loop ends 426, 428, thereby forming the housing 424 of the neckband 420, as illustrated in FIG. 8c.

The experimental diet activity data collection was performed in a soundproof facility in the Department of Biomedical Engineering at Bangladesh University of Engineering and Technology (BUET). The facility consists of a fully soundproof and anechoic recording chamber along with an adjacent control room with a soundproof window between them. Each subject performed various nutritional and other tasks inside the recording chamber in a comfortable sitting position.

Figure 9:
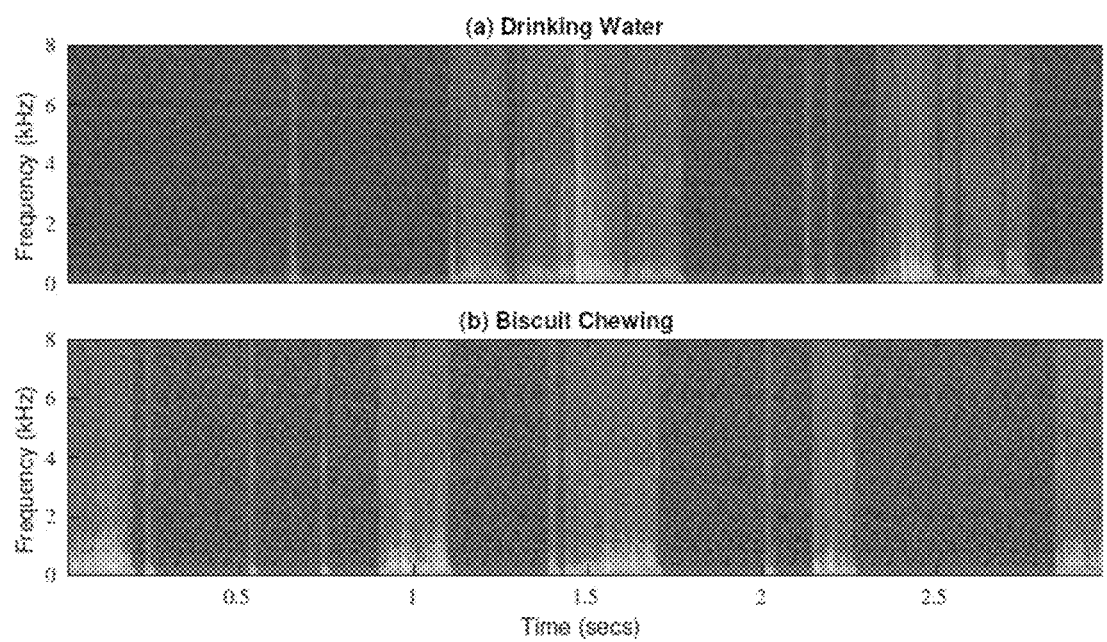
FIG. 9 illustrates spectrograms of drinking water and biscuit chewing recordings acquired using the experimental device.

The diet activity dataset was collected from 20 gender balanced healthy subjects aged between 20 and 25. For drinking activity, each subject consumed 100 ml of water at four different sessions. For solid foods, the subjects were given 15 g of chips (crunchiness), 1 club sandwich (softness), and 2 pieces of chocolate cookies (hardness). To train the algorithm to be robust against other vocal activities, other non-nutritional activities were also recorded, for example speech, coughing, laughter, breathing and dry swallowing. The activities recorded in the dataset are summarized below in Table 3. Exemplary spectrograms of drinking water and biscuit chewing recordings acquired using the experimental device 420 are illustrated in FIG. 9.

TABLE 3

Summary of Activities for Each Subject

Dietary Activity

| Activity | Quantity/Session | #Session |
|----------|------------------|----------|
| Water    | 100 ml           | 4        |
| Biscuit  | 1 pc.            | 2        |
| Chips    | 1 pc.            | 3        |
| Sandwich | 1 pc.            | 1        |

Non-dietary activity

| Activity     | Quantity      |
|--------------|---------------|
| Speech       | 20 sentence   |
| Breathing    | 45 sec        |
| Laughter     | 20 sec        |
| Dry swallow  | 5 times       |
| Coughing     | 10 times      |

To identify frames containing dietary activities, the audio signal was first divided into 40 ms frames and the energy within each frame was calculated. If the short-term energy of a frame was higher than a predefined threshold, it was assumed that a relevant dietary activity is present. The energy threshold was set empirically by observing energy histograms obtained from a data sub set.

Sixty-three dimensional Mel frequency Cepstral Coefficients (MFCC) were used as the first set of short-term features. A 30-channel Mel-filterbank was used, with 21 static coefficients retained (including $C_0$ and log-energy). Next, the delta and acceleration coefficients of the MFCC's are appended. In addition to MFCCs, several spectral, waveform and energy based features were extracted, as summarized in Table 1 above. All of the short-term features were calculated from 40 ms frames with an overlap of 75%. The features were then concatenated to the selected feature set to obtain a 76 dimensional vector.

In order to detect longer-term dietary activities (e.g., chewing), feature parameters were observed over a window of several seconds. In the experimental wearable system 420, segmental features were extracted by calculating several statistical functions from the short-term features within a 3 second window or segment. From each of the 76 dimensional features in Table 1, 7 statistical functions summarized in Table 2 (mean, median, standard deviation, skewness, kurtosis, maximum, and minimum) were calculated to obtain segmental features of dimension 532 from each 3 second window. The experimental real-time implementation also utilized a 3 second audio buffer and provided a classification decision within the 3 second time frame.

The ReliefF method was used to select a subset of features from the 532 dimension segmental feature vectors to reduce the dimensionality of the 532 dimensional segmental feature vectors to a segmental feature vector containing a set of 76 selected features, each of which is a coefficient determined by applying a statistical function to a segment of the short-term features.

The experimental data was tested with several different machine learning algorithms for dietary activity detection from the segmental features extracted from the 3 second windows. The evaluated classifiers include Gaussian mixture model (GMM), linear discriminant analysis (LDA), Naive Bayes (NB), decision tree (DT), k-nearest neighbor (kNN) and random forest (RF). The classifier parameters as used in the experimental embodiments are summarized in Table 4 below.

TABLE 4

Parameters for Experimental Classifiers

| Classifiers | Parameters |
|---|---|
| Gaussian Mixture Model (GMM) | No. of mixture components: 16 |
|  | No. of EM iterations: 50 |
| Linear Discriminant Analysis (LDA) | Kernel: Linear |
|  | Optimization: Bayesian |
| Naive Bayes (NB) | Kernel: Normal Distribution |
|  | Max objective evaluation: 30 |
| Decision Tree (DT) | Max grid division: 10 |
| k-Nearest Neighbour (kNN) | Number of neighbors: 5 |
|  | Neighbour search method: kd-tree |
| Random Forest (RF) | No. of Bags/tree: 76 |
|  | Tree method: Classification |

Figure 10:
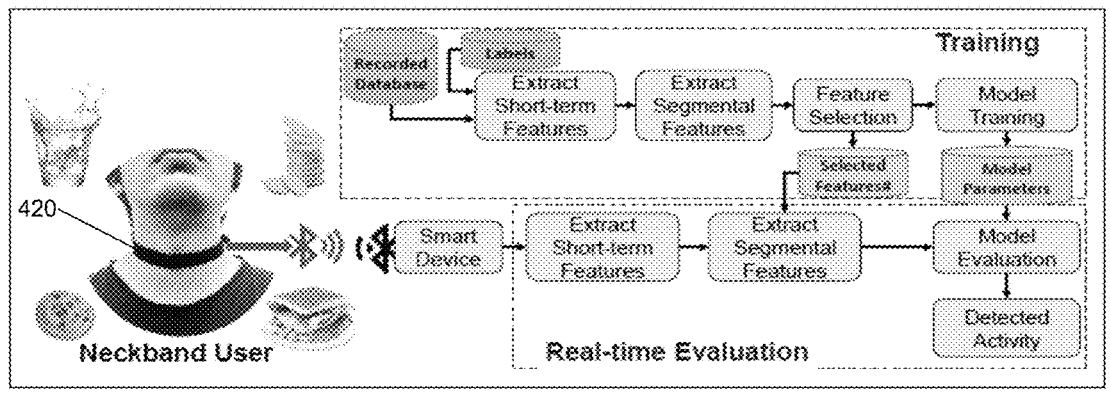
FIG. 10 is a simplified schematic diagram illustrating the relationship between the neckband and the training and evaluation processes.

FIG. 10 illustrates the relationship between the neckband 420 and the training and evaluation processes. In order to monitor the dietary activity in real-time, the neckband 420 was connected to the PC as a Bluetooth® device. A MATLAB application on the computer initiated the device as an audio input and, when the dietary monitoring starts, the application acquired the audio stream from the device on 3 second buffers and notified the user of the detected dietary/non-dietary activity.

To evaluate the effectiveness of the wearable diet activity detection system 420, an experimental setup was devised with a 5-class classification task. The 5 classes included: (i) drinking water (liquid), (ii) eating biscuit (hardness), (iii) eating chips (crunchiness), (iv) eating sandwich (softness), and (v) other non-ingestion activities. A 3-class experimental protocol for was also devised for further experiments, in which the three classes included: (i) drinking (liquid), (ii) chewing (solid food), and (iii) other non-ingestion activities.

In the recorded dataset, the total duration of the dietary activities was much smaller compared to that of the non-dietary activities, creating an imbalance in the training set. To address this issue, the dietary activity features of a diet class were oversampled by several folds to balance the training dataset.

The experiments were set-up over the 20 subjects' data in the form of leave-one-subject-out cross-validation. For performance evaluation, the class-wise precision, recall, F-measure, and also the average of these metrics, were determined over different classes.

First, the feature selection effects were observed for the 5-class classification task. Table 5 shows the averaged classification results with and without feature selection when the RF classifier was used.

TABLE 5

Effect of Feature Selection on 5-Class Task Using RF Classifier

| Features (dimension) | Precision (%) | Recall (%) | F-measure (%) | Acc. (%) |
|---|---|---|---|---|
| Full-set (532) | 57.08 | 54.71 | 54.47 | 86.55 |
| Selected features (76) | 57.23 | 54.02 | 54.07 | 86.53 |

Figure 11:
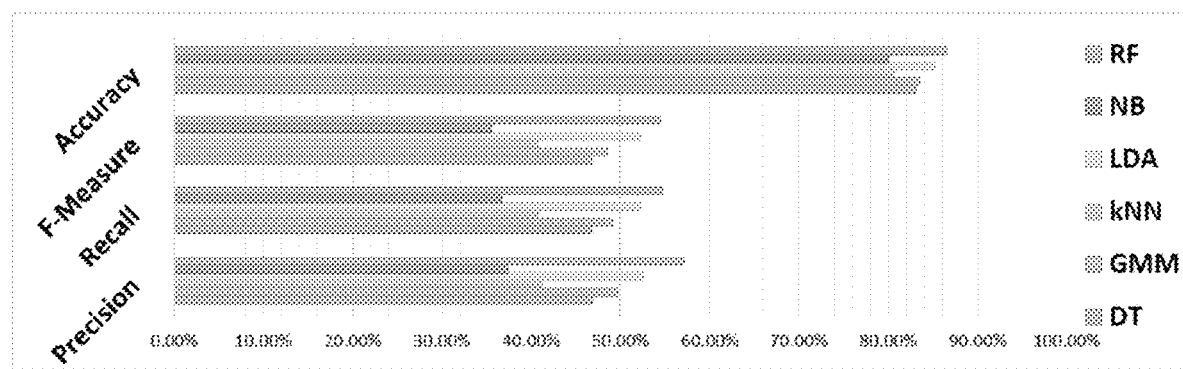
FIG. 11 is a bar graph showing the performance of the different machine learning algorithms from the experiments using in the 5-class classification task.

FIG. 11 illustrates the performance of the different machine learning algorithms from the experiments using in the 5-class classification task. The comparison of performance metrics shows that the RF classifier outperformed the other classifiers in the experimental data sets. Table 6 shows the detailed RF classifier experimental results, illustrating that the RF classifier had an overall accuracy of 86.53% in the 5-class classification experiment.

TABLE 6

5-Class Experimental Results for Random Forest Classifier

| Class | Precision (%) | Recall (%) | F-measure (%) | Accuracy (%) |
|---|---|---|---|---|
| Drinking | 67.70 | 54.47 | 60.37 | 91.99 |
| Biscuit | 52.09 | 76.23 | 61.89 | 74.62 |
| Chips | 42.43 | 18.40 | 25.67 | 82.60 |
| Sandwich | 27.78 | 27.63 | 27.70 | 87.24 |
| Other Activity | 96.13 | 93.38 | 94.74 | 96.20 |
| Average | 57.23 | 54.02 | 54.07 | 86.53 |

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the sprit and scope of this disclosure.

Another experiment was evaluated on the experimental system using a simpler task of classifying between drinking, solid food and other activities. The results of the 3-class experiment using the RF classifier are shown in Table 7, which illustrates overall precision, recall, and F-measure above 80% and the accuracy of 92.49% for this experiment.

TABLE 7

Results on 3-Class Classification Using Random Forest Classifier

| Class | Precision (%) | Recall (%) | F-measure (%) | Accuracy (%) |
|---|---|---|---|---|
| Drinking | 58.61 | 58.02 | 58.31 | 90.71 |
| Solid Food | 89.37 | 94.47 | 91.85 | 91.24 |
| Other Activity | 97.58 | 89.94 | 93.61 | 95.51 |
| Overall | 81.85 | 80.81 | 81.25 | 92.49 |

The Experimental results for both 3-class and 5-class experiments illustrate that the wearable neckband dietary activity monitoring system accurately detects different types of nutritional activities, and, further, adequately distinguishes over other non-ingestion activities (e.g., speaking, coughing, laughing). Additionally, using a more detailed training dataset enables the detection of not only classifications of food, but rather specific foods so as to enable tracking of the nutritional content ingested based on chewing and swallowing ingestion sounds.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the foregoing disclosure.

The invention claimed is:

1. A system for monitoring dietary activity of a user comprising:
   a wearable device comprising at least one audio input unit configured to record an audio sample corresponding to audio from a user's neck;
   a processor configured to execute programmed instructions stored in a memory to:
   obtain an audio sample from the audio input unit of a wearable device;

determine segmental feature values of a set of selected features from the audio sample, the segmental feature values indicative of chewing and swallowing sounds, the determining of the segmental feature values comprising:
  extracting short-term features in the set of selected features from the audio sample, the short-term features including at least one of (i) a delta mel-frequency cepstral coefficient (MFCC), (ii) a delta-delta MFCC, and (iii) a shifted delta cepstral (SDC) coefficient; and
  determining the segmental feature values of the set of selected features from the extracted short-term features;
using a classifier, classify a dietary activity based on the determined segmental feature values of the audio sample; and
generate an output corresponding to the classified dietary activity.

2. The system of claim 1, wherein the audio input unit includes an electret condenser microphone.

3. The system of claim 1, further comprising:
an external device comprising the processor and the memory,
wherein the wearable device further comprises a communication module, and
wherein the processor is further configured to obtain the audio sample via wireless communication with the communication module.

4. The system of claim 1, wherein the processor is arranged in the wearable device.

5. The system of claim 1, wherein the wearable device is a neckband configured to be worn around the user's neck.

6. The system of claim 1, wherein the set of selected features and classifier parameters for the classifier stored in the memory are determined in a machine-learning training process.

7. The system of claim 1, wherein:
the classifier is a random forest classifier;
the determining of the segmental feature values further comprises:
  segmenting the extracted short-term features into segments of a predetermined time duration; and
  applying statistical functions to the extracted short-term features in each segment.

8. The system of claim 7, wherein:
the short-term features further include one or more of: energy entropy, short-term energy, zero crossing rate, spectral flux, spectral crest, spectral skewness, spectral centroid, spectral slope, spectral decrease, spectral spread, spectral rolloff, and spectral flatness; and
the statistical functions include one or more of mean, median, standard deviation, skewness, kurtosis, maximum, and minimum.

9. The system of claim 1, further comprising:
an output device configured to generate a perceptible output, wherein the processor is configured to communicate with the output device to generate the output as the perceptible output.

10. The system of claim 1, wherein the generating of the output includes storing the output in the memory.

11. The system of claim 1, wherein the processor is further configured, before determining the segmental feature values of the set of selected features, to detect whether activity occurs in each frame of the audio sample by comparing an energy of the frame with a predetermined energy threshold.

12. A method of monitoring dietary activity comprising:
obtaining, with a processor, an audio sample from an audio input unit of a wearable device, the audio sample corresponding to audio from a user's neck;
determining, with the processor, segmental feature values of a set of selected features from the audio sample, the segmental feature values indicative of chewing and swallowing sounds, the determining of the segmental feature values comprising:
  extracting short-term features in the set of selected features from the audio sample, the short-term features including at least one of (i) a delta mel-frequency cepstral coefficient (MFCC), (ii) a delta-delta MFCC, and (iii) a shifted delta cepstral (SDC) coefficient; and
  determining the segmental feature values of the set of selected features from the extracted short-term features;
classifying, with the processor, a dietary activity based on the determined segmental feature values of the audio sample; and
generating an output corresponding to the classified dietary activity.

13. The method of claim 12, wherein the audio input unit includes an electret condenser microphone.

14. The method of claim 12, wherein the obtaining of the audio sample includes obtaining the audio sample by wireless communication via a communication module of the wearable device, and the processor is arranged in an external device.

15. The method of claim 12, wherein the processor is mounted in the wearable device.

16. The method of claim 12, wherein the wearable device is a neckband.

17. The method of claim 12, wherein the set of selected features and classifier parameters for the classifier are determined in a machine-learning training process.

18. The method of claim 17, wherein:
the classifier is a random forest classifier;
the determining of the segmental feature values further comprises:
  segmenting the extracted short-term features into segments of a predetermined time duration; and
  applying statistical functions to the extracted short-term features in each segment;
the short-term features further include one or more of: energy entropy, short-term energy, zero crossing rate, spectral flux, spectral crest, spectral skewness, spectral centroid, spectral slope, spectral decrease, spectral spread, spectral rolloff, and spectral flatness; and
the statistical functions include one or more of mean, median, standard deviation, skewness, kurtosis, maximum, and minimum.

19. The method of claim 12, wherein the generating of the output includes generating a perceptible output via an output device.

20. A system for monitoring dietary activity of a user comprising:
a wearable neckband comprising:
  at least one audio input unit comprising an electret condenser microphone configured to record an audio sample corresponding to audio from a user's neck;
  a communication module configured to wirelessly transmit the recorded audio sample to an external device;

an energy storage unit configured to store electrical power for operation of the at least one audio input unit and the communication module; and a housing comprising an elastically deformable fabric in which the at least one audio input unit, the communication module, and the energy storage unit are arranged, the housing including a fastening arrangement at each end of the housing; and the external device, which includes a processor configured to execute programmed instructions stored in a memory to:

obtain the recorded audio sample from the wearable neckband;

determine segmental feature values of a set of selected features from the recorded audio sample, the segmental feature values indicative of chewing and swallowing sounds, the determining of the segmental feature values comprising:

extracting short-term features in the set of selected features from the audio sample, the short-term features including at least one of (i) a delta mel-frequency cepstral coefficient (MFCC), (ii) a delta-delta MFCC, and (iii) a shifted delta cepstral (SDC) coefficient and determining the segmental feature values of the set of selected features from the extracted short-term features;

using a classifier, classify a dietary activity based on the determined segmental feature values of the audio sample; and generate an output corresponding to the classified dietary activity.

\* \* \* \* \*

UNITED STATES PATENT AND TRADEMARK OFFICE
CERTIFICATE OF CORRECTION

PATENT NO. : 10,636,437 B2
APPLICATION NO. : 16/284309
DATED : April 28, 2020
INVENTOR(S) : Taufiq Hasan, Shabnam Ghaffarzadegan and Zhe Feng It is certified that error appears in the above-identified patent and that said Letters Patent is hereby corrected as shown below:

In the Claims

In Claim 20, at Column 21, Line 24, insert a --;-- between the words "coefficient" and "and".

Signed and Sealed this
Twenty-fourth Day of November, 2020

Andrei Iancu
*Director of the United States Patent and Trademark Office*